United States Patent [19]

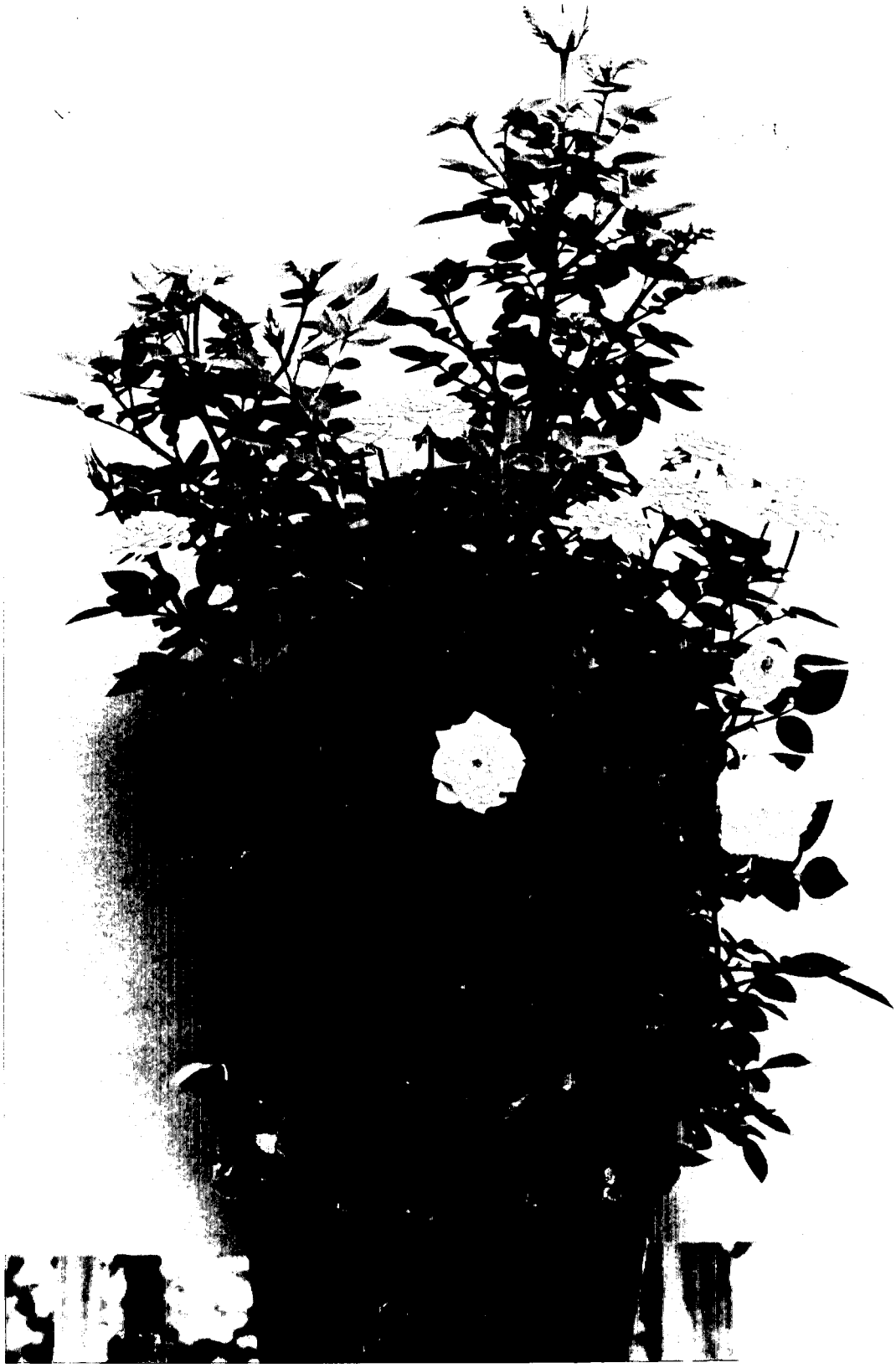

De Ruiter

[11] Patent Number: Plant 5,774

[45] Date of Patent: Jul. 29, 1986

[54] ROSE PLANT-RUIMIOR

[75] Inventor: Gijsbert De Ruiter, Hazerswoude, Netherlands

[73] Assignee: Jackson & Perkins Company, Medford, Oreg.

[21] Appl. No.: 667,634

[22] Filed: Nov. 2, 1984

[51] Int. Cl.[4] ..... A01H 5/00

[52] U.S. Cl. ..... Plt./7

[58] Field of Search ..... Plt./7-10

*Primary Examiner*—James R. Feyrer

*Attorney, Agent, or Firm*—Manford R. Haxton

[57] ABSTRACT

A miniature rose variety having a dwarf, compact plant, producing, when small, buds and blooms of Poppy Red; able to be propagated easily from cuttings and suitable for use as flowering pot plants.

1 Drawing Figure

This present invention relates to a new and distinct variety of rose plant of the miniature class which was originated by crossing the variety Rufin with an unnamed variety.

The primary objective of this breeding was to produce a new rose variety of small size suitable for production of flowering pot plants as well as useful for garden decoration. This objective was substantially achieved along with other desirable improvements as evidenced by the following unique combination of characteristics which are outstanding in the new variety and which distinguish it from its parents as well as from all other varieties of which I am aware:

1. Readily propagated and grown on its own roots by cuttings;
2. Initial blooms when plants are approximately 6" high;
3. Blooms carried in clusters as well as one per stem;
4. Bud and bloom color near Poppy Red (Wilson); and
5. Heavy petal substance causing flower to retain form until dehiscence.

Asexual reproduction of this new variety by cuttings, as performed at Irvine, Calif., and Hazerswoude, Holland, shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with the Wilson's Horticultural Colour Chart except where ordinary dictionary significance of color is indicated:

Parentage:
- *Seed parent.*—Rufin.
- *Pollen parent.*—Unnamed variety.

Classification:
- *Botanical.*—Rosa hybrid.
- *Commercial.*—Miniature.

FLOWER

Observations made from specimens grown in a greenhouse at Irvine, Calif. in August.

Blooming habit: Continuous.

Bud:
- *Size.*—½" when petals start to unfurl.
- *Form.*—Short, blunt top.
- *Color.*—When sepals first divide, Near Poppy Red 16; when half blown, upper side of petals Near Poppy Red 16; lower side of petals Near Poppy Red 16.
- *Sepals.*—Color: Scheeles Green 860. Three appendaged sepals normally appendaged. Two appendaged sepals hairy edged.
- *Receptacle.* Color: Scheeles Green 860. Shape: Narrow cone. Size: Small, slender. Surface: Smooth.
- *Peduncle.*—Length: Short. Surface: Glandular. Color: Light green. Strength: Stiff, erect.

Open bloom:
- *Size.*—Small. Average open size 1".
- *Borne.*—Singly, in clusters, irregular.
- *Stems.*—Short, strong.
- *Form.*—When first open, flat. Permanence: Retains its form to the end.
- *Petalage.*—Number of petals under normal conditions: 40-50.
- *Color.*—Center of flower: Upper side of petals, Near Poppy Red 16; reverse side of petals, Near Poppy Red 16. Base of petals, large area of light yellow. Major color: Poppy Red.
- *Variegations.*—None.
- *Discoloration.*—General tonality at end of first day: Poppy Red 16/1. Third day: Poppy red 16/2.
- *Fragrance.*—None.

Petals:
- *Texture.*—Thick.
- *Shape.*—Near round to oval.
- *Form.*—Edges slightly quilled.
- *Arrangement.*—Imbricated. Petaloids in center, few.
- *Persistence.*—Drop off cleanly.
- *Lastingness.*—On the plant, long. As cut flower, long.

Reproductive parts:
- *Anthers.*—Rarely present.
- *Styles.*—Color: Vegetative and green.
- *Stigmas.*—Color: Rarely present.

PLANT

Form: Bush.

Growth: Vigorous, dwarf, upright.

Foliage: Number of leaflets on normal mid-stem leaves: Usually 7, sometimes 5.

*Size.*—Small.

*Quantity.*—Normal.

*Color.*—New foliage: Light green, suffused lightly with Garnet Brown 00918/3. Old foliage: Normal green.

Leaflets:

*Shape.*—Oval pointed.

*Texture.*—Leathery.

*Edge.*—Serrated.

*Serration.*—Single, small.

*Petiole.*—Rachis: Color: Green. Underside: With long prickles. Upper edges, glandular.

*Stipules.*—Medium, bearded.

*Disease resistance.*—Resistant to mildew, under normal growing conditions at Irvine, Calif.

Wood:

*New wood.*—Color: Light green. Bark: Smooth.

*Old wood.*—Color: Green. Bark: Smooth.

Prickles:

*Quantity.*—On main canes from base: Few. On laterals from main canes: Few.

*Form.*—Straight.

Small prickles:

*Quantity.*—On main stalks, none. On laterals, none.

I claim:

1. A new and distinct variety of rose plant of the miniature class, substantially as herein shown and described, characterized particularly as to novelty by the unique combination of its dwarf, compact plant, producing, when small, buds and blooms of Poppy Red; able to be propagated easily from cuttings and suitable for use as flowering pot plants.

* * * * *